(12) United States Patent
Koganov et al.

(10) Patent No.: US 11,154,492 B2
(45) Date of Patent: Oct. 26, 2021

(54) **BIOACTIVE COMPOSITIONS FROM GINSENG PLANT (*PANAX* SPP.) AND METHODS FOR THEIR PRODUCTION AND USE**

(71) Applicant: ISP INVESTMENTS LLC, Wilmington, DE (US)

(72) Inventors: Michael Koganov, White Plains, NY (US); Olga Dueva-Koganov, White Plains, NY (US); Paul Recht, Pleasantville, NY (US); Artyom Duev, White Plains, NY (US); Li Zhang, Princeton, NJ (US); Steven Micceri, Milford, CT (US); Robert Turner, Peekskill, NY (US)

(73) Assignee: ISP INVESTMENTS LLC, Wilmington, DE (US)

( * ) Notice: Subject to any disclaimer, the term of this patent is extended or adjusted under 35 U.S.C. 154(b) by 254 days.

(21) Appl. No.: 16/070,391

(22) PCT Filed: Jan. 16, 2017

(86) PCT No.: PCT/US2017/013676
§ 371 (c)(1),
(2) Date: Jul. 16, 2018

(87) PCT Pub. No.: WO2017/124075
PCT Pub. Date: Jul. 20, 2017

(65) Prior Publication Data
US 2019/0021984 A1 Jan. 24, 2019

Related U.S. Application Data

(60) Provisional application No. 62/279,242, filed on Jan. 15, 2016.

(51) Int. Cl.
| | |
|---|---|
| *A61K 36/258* | (2006.01) |
| *A61K 36/00* | (2006.01) |
| *A61K 8/9789* | (2017.01) |
| *A61Q 19/00* | (2006.01) |
| *A61Q 19/10* | (2006.01) |

(52) U.S. Cl.
CPC .......... *A61K 8/9789* (2017.08); *A61K 36/258* (2013.01); *A61Q 19/00* (2013.01); *A61K 2800/74* (2013.01); *A61K 2800/75* (2013.01); *A61Q 19/005* (2013.01); *A61Q 19/10* (2013.01)

(58) Field of Classification Search
None
See application file for complete search history.

(56) References Cited

U.S. PATENT DOCUMENTS

| | | | |
|---|---|---|---|
| 2003/0190378 A1* | 10/2003 | Kim | A61K 36/258 424/728 |
| 2013/0287708 A1 | 10/2013 | Silberstein et al. | |
| 2015/0258012 A1 | 9/2015 | Koganov | |

FOREIGN PATENT DOCUMENTS

WO WO 2013/176512 A1 11/2013

OTHER PUBLICATIONS

International Search Report of PCT Application No. PCT/US2017/013676 dated Jul. 20, 2017.

* cited by examiner

*Primary Examiner* — Michael Barker
*Assistant Examiner* — Randall O Winston
(74) *Attorney, Agent, or Firm* — William J. Davis; Nathalie Tietcheu

(57) ABSTRACT

The present invention relates to bioactive compositions (including, for example, bioactive serum fractions and bioactive extracts) derived from ginseng (*Panax* spp.) fresh whole plant, a particular part of the plant (e.g., rhizome, roots, leaves, stems, flowers, fruit) or any combination of these plant parts. The bioactive serum fractions and bioactive extracts are free of or substantially free of pulegone and/or free of or substantially free of proteins. The present invention also provides products comprising the bioactive serum fractions and/or bioactive extracts. The present invention further provides methods of making and using the bioactive serum fractions and/or bioactive extracts. Further, the bioactive serum fractions and bioactive extracts have anti-inflammatory and/or anti-irritant and/or anti-aging activities.

10 Claims, 3 Drawing Sheets

Ginsenoside Rg1

Ginsenoside Rg3

Ginsenoside Rh2

BIOACTIVE COMPOSITIONS FROM GINSENG PLANT (*PANAX* SPP.) AND METHODS FOR THEIR PRODUCTION AND USE

CROSS REFERENCE TO RELATED APPLICATIONS

This application is a U.S. National Phase filing under 35 U.S.C. § 371 of International Application No. PCT/US2017/013676, filed Jan. 16, 2017, and published as WO 2017/124075 A1 on Jul. 20, 2017 which claims benefit of priority from U.S. Provisional Patent Application Ser. No. 62/279,242, filed Jan. 15, 2017. The entire contents of each of the prior applications are incorporated herein by reference in their entirety.

FIELD OF THE INVENTION

The present invention relates to bioactive compositions (including, for example, bioactive serum fractions and bioactive extracts) derived from ginseng (*Panax* spp.) fresh whole plant, a particular part of the plant (e.g., rhizome, roots, leaves, stems, flowers, fruit), or any combination of these plant parts. Further, the bioactive compositions of the present invention (e.g., the bioactive serum fractions and bioactive extracts from ginseng) have anti-inflammatory and/or anti-irritant and/or anti-aging activities.

BACKGROUND OF THE INVENTION

*Panax* spp. definition encompasses closely related plants of the Araliaceae family, including: *Panax quinquefolius* L. or *Panax quinquefolium* (American ginseng); *Panax ginseng* C. A. Meyer (Chinese ginseng, Manchurian ginseng, or Korean ginseng); *Panax japonicus* C. A. Meyer (chikusetsu ninjin or Japanese ginseng), and *Panax pseudoginseng* Wall (notoginseng, San-ch'i ginseng, and Himalayan ginseng). *Panax* spp. term is often used to designate several closely related species within this genus that are used in cosmetics and in nutraceuticals. In should be noted that *P. ginseng, P. quinquefolius, P. japonicus*, and *P. pseudoginseng* are being used in cosmetics under their own individual names, or all as *P. ginseng*, or interchangeably under the generic name "ginseng". A discussion in the personal care industry is currently taking place regarding: if there is or if there is not a real difference among *Panax* spp. plants used in cosmetic application.

In general, ginseng or ginseng root refers to the dried root of the *P. ginseng, P. quinquefolius, P. japonicas*, and *P. pseudoginseng* plants. The plants may be from wild or cultivated sources [Hsu P C. Commercial production of American ginseng (*Panax quinquefolius* L.). *Native Plants Journal*. 2002; 3: (2): 106-108].

If the root is raw or dried, then it is referred to as "white" ginseng. If root has been steamed and dried before extraction or pulverizing, it is referred to as "red" ginseng because of a change in coloring [World Health Organization (WHO). WHO Monographs on Selected Medicinal Plants—Volume 1. 1999. pp. 168 Geneva: World Health Organization (WHO)].

If root is steamed and dried 9 times, the coloring darkens more and the product is referred to as "black ginseng" [Ministry of Health, Labor and Welfare. *Ginseng*—Japanese Pharmacopoeia English Edition, 2007] and [Yun B S, Lee M R, Oh C J, Cho J H, Wang C Y, Gu U, Mo E K, and Sung C K. Characterization of black ginseng extract with acetyl- and butyrylcholinesterase inhibitory and antioxidant activities. *Journal of Ginseng Research*. 2010; 34:(4):248-254].

Various extraction methods used in conjunction with ginseng (*Panax* spp.) were described in the literature; and the root is most widely used part of *Panax* spp. for extraction purpose.

The history of scientific research on ginseng dates back to 1854 when Garriques, an American scientist, isolated a saponin from ginseng. However, the actual introduction of ginseng to the West happened after World War II. The chemical structures of several ginseng saponins were characterized in the late 1960s and further accelerated scientific research on ginseng. Saponin components are triterpenoidal dammarane glycosides, named ginsenosides Rx—according to their mobility on TLC plates, with polarity decreasing from index "a" to "h" [Jong Dae Park, Dong Kwon Rhee & You Hui Lee. Biological activities and chemistry of saponins from *Panax ginseng* C. A. Meyer Phytochemistry Reviews (2005) 4: 159-175].

Saponins (or ginsenosides), a sweet-bitter material, usually exist in plants in the form of glycosides known as "saponin glycosides" Saponin glycosides are macromolecules and are composed of a "sugar" (glycone) and a "non-sugar" (aglycone). The aglycone is also called genin. The aglycones of ginseng are called sapogenins [Hou J P. The chemical constituents of ginseng plants. *Comparative medicine East and West*. 1977; 5:(2):123-145]. More than 60 different ginsenosides have been isolated from the leaves, stems, berries, and roots of various *Panax* spp. [Chang Y S, Seo E K, Gyllenhaal C, Block KI (2003) *Panax ginseng*: a role in cancer therapy? Integr Cancer Ther 2:13-33].

Since different parts of ginseng plant contain different ginsenosides, administration of one part of the plant could result in pharmacological actions different from those caused by administration of another part [Attele A S, Wu J A, Yuan C S (1999) Ginseng pharmacology: multiple constituents and multiple actions. Biochem Pharmacol 58:1685-1693].

The roots of the ginseng were used as herbal medicine in Asia for over two thousand years. It is purported to possess antioxidant, anticarcinogenic, anti-inflammatory, antihypertensive and anti-diabetic properties. The pharmacologically active compounds behind the claims of ginseng's efficacy usually are attributed to ginsenosides; their underlying mechanism of action, although not entirely elucidated, appears to be similar to that of steroid hormones. Each ginseng species has its own set of ginsenosides. Ginsenosides are a diverse group of steroidal saponins with a four ring-like steroid structure that are concentrated primarily in the roots of ginseng plants. The American ginseng and the Korean ginseng both have similar ginsenosides, the American ginseng (*Panax quinquefolius*) is said to be richer in Rb1 group ginsenosides whereas the Korean ginseng (*Panax ginseng*) is richer in ginsenosides of the Rg1 group. It is noteworthy that those attributes depend on the age of the roots when the plant was harvested, the storage conditions, and the duration of storage.

Analysis of commercially available *panax ginseng* root preparations (both powder and liquid) show that these vary widely in the amount of saponins (Rb1, Rb2, Rc, Rd, Re, Rf, and Rg1) [Harkey M R, Henderson G L, Gershwin M E, Stern J S, and Hackman R M. Variability in commercial ginseng products: An analysis of 25 preparations. Am J Clin Nutr. 2001; 73:1101-1106]. *Panax ginseng* root extract is reported to have a ginsenoside content of 0.2-0.3% [Personal Care Products Council. 7-6-2011. Supplier Information on

*Panax ginseng* Root Extract. Unpublished data submitted by the Personal Care Products Council].

Fresh roots have yielded higher amounts of panaxatriol (Re+Rf+Rg1+Rg2+Rh1; 2.8 mg/g DW) and panaxadiol (Rb1+Rb2+Rb3+Rc+Rd+Rg3; 16 mg/g DW) saponins compared to dried roots and powdered roots [Kim S-J, Murthy H N, Hahn E-J, Lee H L, and Paek K-Y. Parameters affecting the extraction of ginsenosides from the adventitious roots of ginseng (*Panax ginseng* C. A. Meyer). Separation and Purification Technology. 2007; 56:401-406]. One reference describes the extraction of the root performed by percolation with aqueous alcohol solution (60%) and then concentration under vacuum to dryness or percolation with propylene glycol followed by concentration under vacuum [Committee of Experts on Cosmetic Products, Patri F, and Silano V. Plants in cosmetics. 1 ed. Germany: Coucil of Europe Publishing, 2002]. The solvents for the root extract may include propylene glycol, propylene glycol+water, propylene glycol dicaprylate/dicaprate, butylene glycol, ethanol, ethanol+water, glycerin+water, caprylic/capric triglyceride, or *Helianthus annuus* (sunflower) seed oil [Personal Care Products Council. 7-6-2011. Supplier Information on *Panax ginseng* Root Extract. Unpublished data submitted by the Personal Care Products Council].

One supplier reported "aging" the *panax ginseng* root in ethanol and butylene glycol (70% aqueous) for 6 weeks before filtering and evaporating the ethanol. This procedure results in a total of 4.61±0.98 mg/g dry weight ginsenosides (2.75±0.7 triol, 1.86±0.3 diol, 0.73±0.11 mg/g diol/triol). One manufacturer reported the extraction process grinds the whole dried red ginseng and places the ground ginseng root into an extraction solvent of ethanol (70%) for 12 h at 20-25° C. The solvent is then filtered and evaporated to remove the ethanol to <1%. The product is then centrifuged, dried, and sterilized [Radiant. 2011. Planoxia-RG (*Panax ginseng* Root Extract). Unpublished data submitted by the Personal Care Products Council]. It is known that saponin glycosides are extractable from the ginseng roots with hot water or alcohols [Hou J P. The chemical constituents of ginseng plants. Comparative medicine East and West. 1977; 5:(2):123-145]. Saponins may be extracted from fresh raw *P. quinquefolium* root using methanol (30%-100%) at room temperature, over heat, or under microwave conditions. Each of these processes gives a different ratio of saponins (i.e., Re, Fb1, mRb1) in the extract [Dai J and Orsat V. Extraction of ginsenosides from American ginseng (*Panax quinquefolium* L.) root. International Journal of Food Engineering. 2010; 6:(3): Article 3].

Variation in yield and type of yield also depends on sample size, extraction time, sample to solvent ratio, and solvent concentration. Temperature influences the extraction kinetics, solvent viscosities, extraction efficiencies, and overall recoveries in ultrahigh-pressure extraction. Using 70% aqueous ethanol at 200 MPa, 60° C. was optimal for saponin yields. Other temperatures led to a decreased yield of saponin compounds [Chen R, Meng F, Zhang S, and Liu Z. Effects of ultrahigh pressure extraction conditions on yields and antioxidant activity of ginsenoside from ginseng. Separation and Purification Technology. 2009; 66:340-346].

Figure 1:
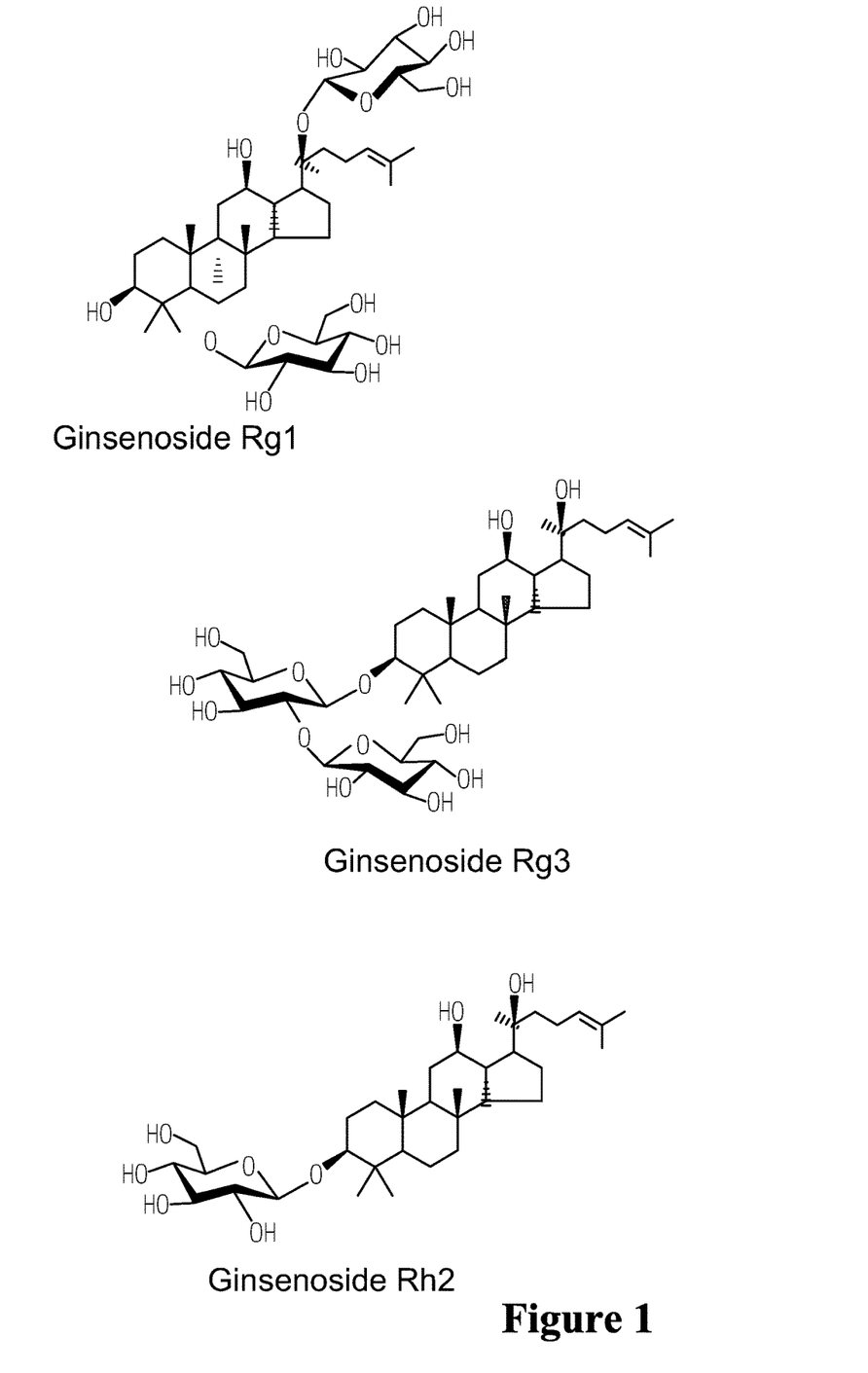
FIG. 1 illustrates the chemical structures of several key saponins found in ginseng (*Panax* spp.). The saponins shown in FIG. 1 include Ginsenoside Rg1, Ginsenoside Rg3, and Ginsenoside Rh2.

The chemical structures of several key saponins (e.g., Ginsenoside Rg1, Ginsenoside Rg3, and Ginsenoside Rh2), which are beneficial biologically active constituents found in ginseng (*Panax* spp.), are shown in FIG. 1.

In addition to the beneficial constituents, e.g. ginsenosides found in ginseng (*Panax* spp.), there are certain undesirable components of concern including pulegone and protein.

Pulegone is a monoterpene ketone with known and well-documented toxicity; its two enantiomeric forms occur in nature, the R-(+)-enantiomer being the most abundant in certain essential oils. Pulegone was reported as a constituent of *P. quinquefolius*. In food, the levels of pulegone are limited to 25 ppm and in alcoholic beverages—to 100 ppm [Corrado L. Galli, Giovanni Galli, Elena Tragni, Donatella Caruso and Alberto Fiecch. Quantitative analysis of α,β-thujone, pulegone, safrole, coumarin and β-asarone in alcoholic beverages by selected-ion monitoring. Journal of Applied Toxicology. Volume 4, Issue 5, pages 273-276, October 1984].

Because of the known toxicity of pulegone, in an earlier safety assessment of peppermint oil, the safety of the ingredient was assured only when the levels of pulegone were limited to ≤1% in the ingredient [Andersen F A. Final report of the safety assessment of *Mentha piperita* (peppermint) oil, *Mentha piperita* (peppermint) leaf extract, *Mentha piperita* (peppermint) leaf, and *Mentha piperita* (peppermint) water. International Journal of Toxicology. 2001; 20:(Suppl. 3):61-73].

Proteins including those in bioactive ingredients for topical applications can cause protein related contact dermatitis in sensitive individuals. Shortly after contact with the causative proteinaceous material, such individuals can experience symptoms such as acute urticarial or vesicular eruption on the skin, often accompanied by pruritus, burning, and/or stinging [V. Janssens, et al., "Protein contact dermatitis: myth or reality?", British Journal of Dermatology 1995; 132: 1-6].

The above references indicate that if they are present in plant derived bioactive compositions (ingredients) at certain concentrations, both types of compounds, pulegone and proteins, could be considered as unwanted compounds of concern.

Overall, ginseng (*Panax* spp.) is an extremely potent and valuable source of bioactive compositions (ingredients), especially if certain unwanted components of concern (e.g., pulegone and proteins) are completely removed from or their concentrations are substantially reduced in these compositions.

Thus, it is highly desirable to obtain bioactive compositions from Ginseng (*Panax* spp.) that contain as little pulegone and as little protein as possible. A significant task exists in simultaneously removing or substantially reducing the concentrations of pulegone and protein in the bioactive compositions obtained from ginseng (*Panax* spp.)—while maintaining high concentrations of desirable compounds and high biological activity of these compositions.

The present invention is directed toward addressing these and other deficiencies in the prior art.

SUMMARY OF THE INVENTION

The present invention relates to bioactive compositions (including, for example, bioactive serum fractions and bioactive extracts) derived from ginseng (*Panax* spp.) fresh whole plant, a particular part of the plant (rhizome, roots, leaves, stems, flowers, fruit), or any combination of these plant parts. Further, the bioactive compositions of the present invention (e.g., the bioactive serum fractions and bioactive extracts derived from ginseng) have anti-inflammatory and/or anti-irritant and/or anti-aging activities.

More particularly, in certain embodiments, the bioactive compositions (ingredients) of the present invention are free of or substantially free of pulegone and protein.

Further, the bioactive compositions (ingredients) have anti-inflammatory and/or anti-aging and/or anti-irritant activities.

The present invention also relates to a method for isolating bioactive compositions (ingredients) that are free or substantially free of pulegone and proteins from ginseng (*Panax* spp.) fresh whole plant, particular parts of the plant (e.g., rhizome, roots, leaves, stems, flowers, fruit), or any combination of these plant parts.

The present invention also relates to various uses of the bioactive compositions described herein, including, without limitation, personal care uses.

BRIEF DESCRIPTION OF THE DRAWINGS

For the purpose of illustrating aspects of the present invention, there are depicted in the drawings certain embodiments of the invention. It is believed that the present invention will be better understood from the following description taken in conjunction with the accompanying drawings. The referenced drawings are not to be construed as limiting the scope of present invention.

DETAILED DESCRIPTION OF THE INVENTION

It has now been discovered that bioactive compositions (including, for example, bioactive serum fractions and bioactive extracts) derived from ginseng (*Panax* spp.) fresh whole plant, particular parts of the plant (e.g., rhizome, roots, leaves, stems, flowers, fruit), or any combination of these plant parts, have anti-inflammatory and/or anti-irritant and/or anti-aging activities.

In certain embodiments, the bioactive serum fractions and bioactive extracts are free of or substantially free of pulegone and/or free of or substantially free of proteins.

The present invention also provides products and compositions comprising the bioactive serum fractions and/or bioactive extracts.

The present invention further provides methods of making the bioactive serum fractions and/or bioactive extracts.

The products and compositions of the present invention can comprise, consist essentially of, or consist of, the essential components (e.g., the bioactive serum fractions and bioactive extracts derived from ginseng (*Panax* spp.)), as well as optional ingredients described herein. The essential components can include, without limitation, the bioactive serum fractions and bioactive extracts derived from ginseng (*Panax* spp.) fresh whole plant, particular parts of the plant (e.g., rhizome, roots, leaves, stems, flowers, fruit), or any combination of these plant parts. As used herein, "consisting essentially of" means that the composition or component may include additional ingredients, but only if the additional ingredients do not materially alter the basic and novel characteristics of the claimed compositions or methods.

Definitions

"Fresh Ginseng" refers to plants of *Panax* genus (*Panax* spp.) harvested and transported in a way enabling them to significantly retain viability compared to unharvested plant. The viability here is defined as photosynthetic functionality of electron transfer system in photosystems II and I, and ATP synthesis. Viability is indicated by quantum yield determined by measuring chlorophyll fluorescence of leaves. Further processing can be performed upon the whole plant, a part of a plant, e.g., rhizome, roots, leaves, stems, flowers, fruit (berries) or any combination of parts of a plant.

"Cleaning" refers to removal of debris from fresh ginseng prior to further processing, in a way that avoids injury to the plant, or removal of valuable components. For example, it can be performed by low-pressure rinsing with potable water under conditions where runoff water wash would not noticeably contain plant pigments. Excess wash water is then removed from the washed plants.

"Maceration" refers to rendering fresh ginseng into smaller particles to disrupt its integrity and ease the following expelling of liquid intracellular dispersion. Examples of suitable maceration implements include, but are not limited to, devices such as a crusher, a grinder, or a mill (e.g., knife mill, hammer mill, etc.). To prevent temperature-induced degradation of plant material, maceration step can include temperature monitoring and selection of maceration parameters ensuring that there is no significant rise in temperature of plant material during this step.

"Pressing" refers to separating liquid material from fresh ginseng by application of mechanical force. This includes, but is not limited to, techniques such as draining by ambient gravity, pressing by a heavy object, centrifugal force from a rotary expeller, pressure from piston of a hydraulic press, or rollers or a screw of appropriate type of press.

"Press-Cake" refers to fiber-enriched solid and/or semi-solid fraction of fresh ginseng from which the liquid intracellular dispersion has been removed by pressing.

"Intracellular Dispersion" refers to liquid material expelled by pressing fresh ginseng. Resulting liquid contains dispersed solid and/or semi-solid particles and possible droplets of water-immiscible liquids of a variety of sizes (collectively referred to as particles), in contiguous aqueous medium. The particles are mainly comprised of plant cell organelles, organelle fragments, and residual fiber-enriched material. The aqueous medium is mainly comprised of cytosol and vacuole contents.

"Adjustment" refers to alteration of activities of hydroxide and hydronium ions in aqueous medium of intracellular dispersion or aqueous fractions produced by further processing of intracellular dispersion, with activity of hydronium ion remaining within range found in viable plant cells (e.g. between pH 3 and pH 8). This alteration can be accomplished by, for example, an electromembrane process (e.g. being passed through an electrodialysis chamber with bipolar membranes), or by addition of an acid or an alkali. Adjustment parameters are selected to be sufficient for a particular change in physico-chemical parameters, such as $^1$H-NMR spin-spin relaxation time ($\tau_2$), or pH, or Work Function value, or surface potential at electrolyte-air interface. Such adjustments facilitate following destabilization and/or separation steps; or create conditions for proper preservation and stabilization.

"Adjustment 1", "Adjustment 2", "Adjustment 3" refer to respective steps of the process carried out with their respective parameters.

"Destabilization" refers to treating adjusted intracellular dispersion using electromagnetic waves for transiently modifying physical properties (such as $\varepsilon'_0$ which is the real component of low-frequency dielectric constant). It was unexpectedly found that particular modifications degrade stability of intracellular dispersion by causing agglomeration and/or aggregation of particles into assemblies which are sufficiently large and stable to enable and/or improve following separation into fractions with certain desirable properties.

"Separation" refers to separating solid and/or semisolid particles and non-aqueous liquid droplets from aqueous liquid by exploiting density and/or size of particles. This includes but is not limited to techniques such as straining, filtration (including filtration utilizing a pressure gradient), skimming, sedimentation by ambient gravity, decanting, centrifugation, or some combination of the above. Continuous flow mechanical separation has been used, but this does not exclude batch processing. "Separation 1" and "Separation 2" refer to respective steps of the process carried out with respective parameters.

"Supernatant" refers to aqueous material from which particles have been separated. "Supernatant 1" and "Supernatant 2" refer to supernatants resulting from respective separation steps of the process.

"Precipitate" refers to particles from which aqueous material has been separated. "Precipitate 1" and "Precipitate 2" refer to precipitates resulting from respective separation steps of the process.

"Preservatives and Stabilizers" refers to substances which, when added to a fraction of fresh ginseng, protect it against expected environmental challenges such as temperature, atmosphere (e.g. oxygen), light, and microorganisms. Particular suitable substances can include, without limitation, a preservative, a stabilizer and/or mixtures thereof. This does not exclude possibility of providing such protection without preservatives and stabilizers, via particular processing and packaging techniques.

"Serum Fraction" refers to Supernatant 2 subjected to Adjustment 3 and mixed with preservatives and stabilizers to create a finished ingredient protected against expected environmental challenges of transport, storage, and use.

"Application", as used in reference to a composition, means to apply or spread the compositions of the present invention onto a mammal skin surface such as the epidermis.

The term "cosmetically acceptable" refers to bioactive ingredients, formulations, cosmetically active agents, or inert ingredients that are suitable for use in contact with mammalian tissues (e.g., the skin of humans), including topical applications, without undue toxicity, incompatibility, instability, irritation, allergic response, and the like, commensurate with a reasonable benefit/risk ratio.

"Dermatologically acceptable" means that the compositions or components described are suitable for use in contact with human keratinous tissue without undue toxicity, incompatibility, instability, allergic response, and the like.

"Topical" refers to a composition that is intended to be applied to a bodily surface such as skin or hair.

As used herein, the term "topical application" generally refers to techniques relating to directly laying on or spreading the bioactive ingredients of the present invention or formulations containing these bioactive ingredients onto the outer skin using, e.g., by use of the hands or an applicator such as a wipe.

As used herein, the term "acceptable in functional food and beverage products" refers to bioactive ingredients, formulations or inert ingredients that are suitable for internal use without undue toxicity, incompatibility, instability, irritation, allergic response, and the like, commensurate with a reasonable benefit/risk ratio.

The present invention provides a commercially viable process for removing or substantially reducing the pulegone and protein content in bioactive ingredients obtained from ginseng (*Panax* spp.).

More particularly, in certain embodiments, the bioactive compositions (ingredients) of the present invention are free of or substantially free of pulegone and protein.

As used herein, "substantially free of proteins" means less than 0.675% total protein content, and more preferably less than 0.500% total protein content determined by hydrolyzed and un-hydrolyzed amino acid analysis conducted on Hitachi L-8900 amino acid analyzer.

As used herein, "substantially free of pulegone" means less than 100 ppm of pulegone, and more preferably, less than 25 ppm of pulegone. In determining pulegone content, one of ordinary skill in the art can use the method described in Corrado L. Galli, Giovanni Galli, Elena Tragni, Donatella Caruso and Alberto Fiecch, Quantitative analysis of α,β-thujone, pulegone, safrole, coumarin and β-asarone in alcoholic beverages by selected-ion monitoring, *Journal of Applied Toxicology*, Volume 4, Issue 5, pages 273-276, October 1984.

"Actives" means compounds that, when applied to keratinous tissue and/or a target portion of keratinous tissue, provide a benefit or improvement to the keratinous tissue. The actives herein can be skin care actives, hair care actives, or a combination thereof.

"Apply" or "application", as used in reference to a composition, means to apply or spread the compositions of the present invention onto a human skin surface such as the epidermis.

"Delivery enhancement device" means any device that increases the amount of active ingredient (e.g., Ginseng extract/serum fraction) applied to and/or into the skin relative to the amount of active ingredient that is delivered without using the device.

"Effective amount" means an amount of a compound or composition sufficient to significantly induce a positive benefit to keratinous tissue, such as a health, appearance, and/or feel benefit, including independently or in combination the benefits disclosed herein, but low enough to avoid serious side effects (i.e., to provide a reasonable benefit to risk ratio, within the scope of sound judgment of the skilled artisan). An "effective amount" is an amount of the bioactive composition of the present invention sufficient to regulate a desired condition of mammalian keratinous tissue when topically applied thereto in a personal care composition.

"Hair care composition" refers to a composition for regulating and/or improving a hair condition. Some non-limiting examples of hair-care compositions include shampoos and hair conditioners.

"Hair conditioning agent" includes cationic surfactants, high melting point fatty compounds, silicone compounds, and mixtures thereof that provide a conditioning benefit to hair. Hair care compositions that include a hair conditioning agent may be referred to as "hair conditioners." However, it is to be appreciated that shampoos may also include a hair conditioning agent.

"Keratinous tissue" refers to keratin-containing layers disposed as the outermost protective covering of mammals which includes, but is not limited to, skin, hair, nails, cuticles, etc.

"Skin-care composition" refers to topical personal care compositions for regulating and/or improving a skin condition. Some nonlimiting examples of skin-care compositions include skin creams, shave prep compositions, moisturizers, lotions, and body washes.

"Shampoo" refers to a hair care composition that includes a combination of a detersive surfactant and a dermatologically acceptable carrier.

"Shave prep composition" refers to a topical personal care composition that is applied before, during, and/or after shaving. "Shaving" refers to the removal of facial or body hair with a razor or similar device. Examples of shave prep compositions include shaving creams, gels, and foams.

Methods for Isolating Bioactive Fractions and Extracts from Whole Fresh Ginseng Plant (*Panax* Spp.)

In one aspect, the present invention provides a method for isolating bioactive serum fractions and bioactive extracts from whole fresh ginseng plants including rhizome, roots, stems, leaves, flowers, and fruit (berries) to produce bioactive fractions in accordance with the present invention.

The present invention also allows for the standardization of initial plant material properties to improve reproducibility of bioactive (fractions) ingredients by exploring uniform conditions for ginseng (*Panax* spp.) cultivation and harvesting.

Figure 2:
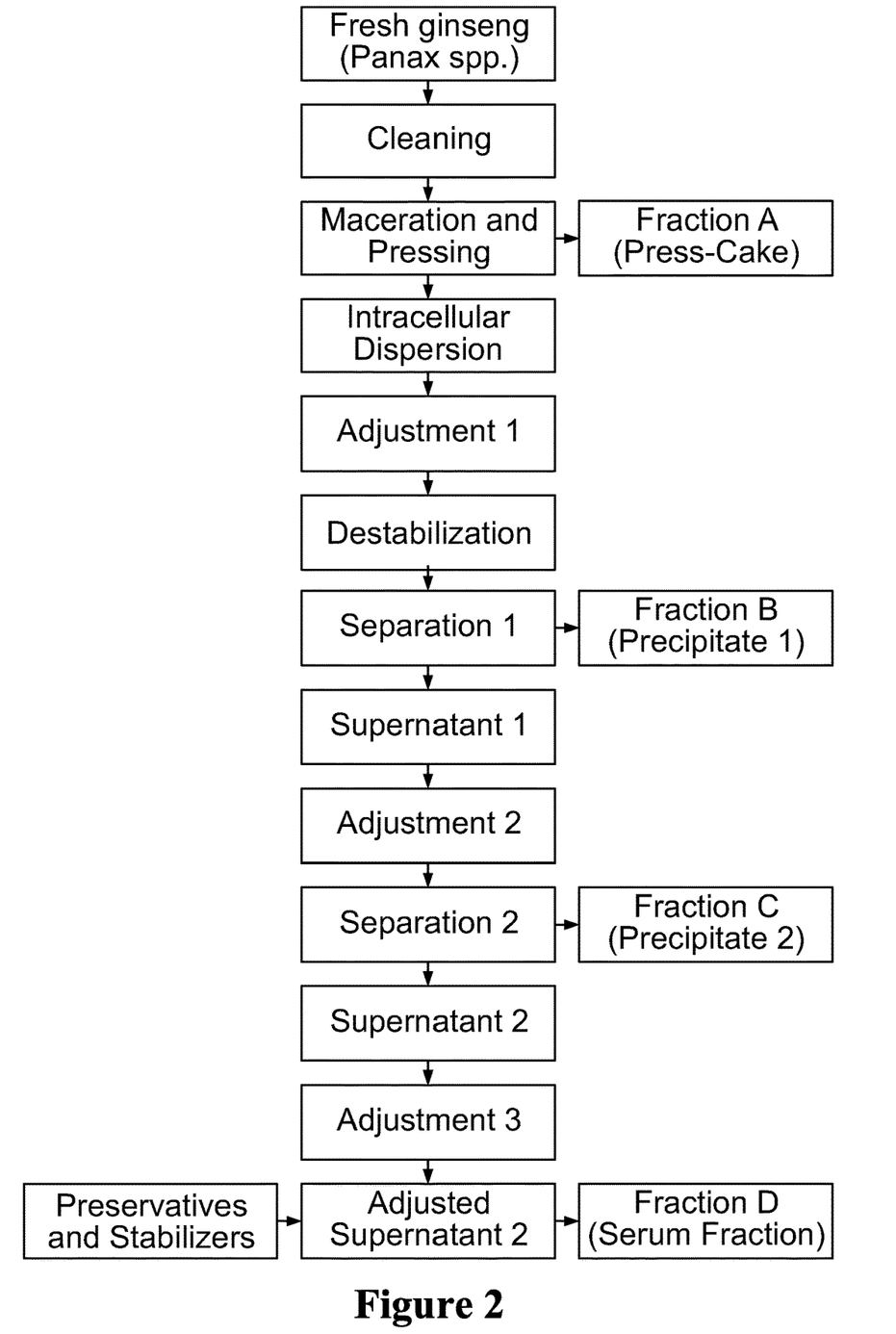
FIG. 2 is a schematic of one embodiment of a process of the present invention for preparing bioactive fractions derived from whole ginseng (*Panax* spp.) plant.

Reference is made to FIG. 2, which is a schematic of one embodiment of a method for processing whole fresh ginseng plants, including rhizome, roots, stems, leaves, flowers, and fruit (berries), to produce bioactive fractions in accordance with the present invention.

In one embodiment of the process of the present invention, ginseng plants were cultivated over four growing seasons. Whole mature cultivated Ginseng plants were dug from the soil when they reached the phase of growth with ripe berries. Collected plants were immediately cleaned with water. Viability of the collected plants was tested utilizing an OS5p multi-mode chlorophyll fluorometer (Opti-Sciences Inc, Hudson, N.H., USA).

In one embodiment of present invention, after maceration and pressing of whole live Ginseng plants the yield of Fraction A (Press-Cake) was between 35% and 55% (w/w) and intracellular dispersion contained from 8% to 12% dry matter.

In the embodiments described below, the value of real component of low-frequency dielectric constant ($\varepsilon'_0$) was determined using broadband dielectric spectroscopy data obtained via equipment and software from Agilent Technologies: PNA-L Network Analyzer N5230C with 85070E dielectric probe kit, N4693-60001 electronic calibration module, and 85070 software. The calculation was performed according to method described in the article [Cole, K. S., & Cole, R. H. (1941). Dispersion and absorption in dielectrics I. Alternating current characteristics. The Journal of Chemical Physics, 9(4), 341-351].

In one embodiment of present invention, "Adjustment 1" is achieved by titration of intracellular dispersion with, e.g., acid to pH=3.0. In another embodiment "Adjustment 1" is achieved by treatment of intracellular dispersion in bipolar electrodialysis chamber enabling to decrease $^1$H-NMR spin-spin relaxation time ($\tau_2$) of intracellular dispersion by about 30 milliseconds (for example from 84 ms to 56 ms) as determined using Acorn Area instrument (Xigo Nanotools, Bethlehem, Pa., USA).

In one embodiment of present invention, $\varepsilon'_0$ of intracellular dispersion was decreased by about 10 F/m (from 80 F/m to 70 F/m).

In another embodiment of present invention, $\varepsilon'_0$ of intracellular dispersion was decreased by about 30 F/m (from 80 F/m to 50 F/m).

It was unexpectedly found that these modifications degrade stability of intracellular dispersion causing agglomeration and/or aggregation of particles (i.e., organelles, organelle fragments, residual fibrous material) into assemblies which are sufficiently large and stable to enable and/or improve mechanical separation to "Supernatant 1" and "Fraction B (Precipitate 1)".

In one embodiment of present invention, "Supernatant 1" has turbidity below about 40 NTU. Fraction B (Precipitate 2) contains about 15.0% to 25.0% dry matter.

In another embodiment of present invention, Fraction B (Precipitate 2) has Work Function value between about 4000 meV and 4200 meV.

Continuous flow destabilizing treatment has been used, but this does not exclude batch processing. Treatment duration and its intensity were applied to produce post-destabilization supernatant and precipitate having certain desirable properties.

In one embodiment of present invention, "Adjustment 2" is achieved by increase of pH level in "Supernatant 1" by titration with, for example, alkali to pH=8.0. In another embodiment, "Adjustment 2" is achieved by treatment of "Supernatant 1" in bipolar electrodialysis chamber enabling to increase $^1$H-NMR spin-spin relaxation time ($\tau_2$) of Supernatant 1 by, for example about 475 milliseconds (from 95 ms to 570 ms).

In another embodiment of present invention, "Adjustment 2" is achieved by treatment of "Supernatant 1" in bipolar electrodialysis chamber enabling to increase its surface potential on electrolyte-air interphase by, for example, about 125 mV (from 250 mV to 375 mV).

As used herein and in the process illustrated in FIG. 2, the term "Separation 2" refers to mechanical separation of adjusted Supernatant 1 to "Supernatant 2" and "Fraction C (Precipitate 2)".

In one embodiment of present invention, "Fraction C (Precipitate 2)" contains about 10.0% to 20.0% dry matter. In another embodiment of present invention, "Fraction C (Precipitate 2)" has Work Function value between about 4000 meV and 4200 meV.

As used herein and in the process illustrated in FIG. 2, "Adjustment 3" is achieved by decrease of pH level in "Supernatant 2" by titration with acid, for example, to pH about 3.5.

In another embodiment, "Adjustment 3" is achieved by treatment of "Supernatant 2" in bipolar electrodialysis chamber enabling to decrease $^1$H-NMR spin-spin relaxation time ($\tau_2$) of "Supernatant 2" by, for example, about 190 milliseconds (from 540 ms to 350 ms).

In another embodiment of present invention, "Adjustment 3" is achieved by treatment of "Supernatant 2" in bipolar electrodialysis chamber enabling to decrease its surface potential on electrolyte-air interphase by, for example, about 220 mV (from 700 mV to 480 mV).

As used herein and in the process illustrated in FIG. 2, the term "Adjusted Supernatant 2" refers to material obtained after "Adjustment 3" and mixed with "Preservatives and Stabilizers".

As used herein and in the process illustrated in FIG. 2, the term "Fraction D (Serum Fraction)" refers to serum with added appropriate preservatives and/or stabilizers to protect composition of the ingredient against expected environmental challenges such as temperature, atmosphere (e.g., oxygen), light, and microorganisms. Serum is mixed with at least one preservative, at least one antioxidant and at least one stabilizer to yield a finished ingredient, or combination of thereof. Particular suitable stabilizing agents can include, without limitation, a preservative, a stabilizer and/or mixtures thereof. Suitable preservatives, antioxidants and stabilizers for use in the present invention include, but are not limited to tetrasodium EDTA, disodium EDTA, potassium sorbate, sodium benzoate, sodium metabisulfite, sodium methylparaben, glycerin, propylene glycol, di-propylene glycol, butylene glycol, pentylene glycol, hexylene glycol, and caprylyl glycol.

This does not exclude possibility of an ingredient free of preservatives and stabilizers being created by using particular processing and packaging techniques.

In one embodiment of present invention Fraction D (Serum Fraction) contains from 6.5% to 8.5% dry matter.

In another embodiment—finished ingredients could be also created based on water or solvent extraction of Fractions A, B or C.

The isolated finished ingredients can be further concentrated and then stabilized for further utilization in skin care for topical, oral and functional drink and food applications. The finished ingredients of the present invention can further be included in delivery systems that are commonly used in the art.

The bioactive ingredients of the present invention are either cosmetically acceptable and/or acceptable in functional food and beverage products.

It was unexpectedly found that the process described herein produced finished ingredients with multifunctional biological activities that are either free of or substantially free of pulegone and proteins.

The formulations containing the bioactive fractions (ingredients) of the present invention may be prepared using methodologies that are well known by one of ordinary skill in the relevant art.

Formulations of Ginseng (*Panax* Spp.) Bioactive Compositions (Serum Fractions) or Extracts The present invention also relates to a bioactive formulation suitable for topical application to mammalian skin and/or hair. The formulation can be a leave-on product such as, for example, a cream, dressing, gel, lotion, ointment, liquid, a spray applicator, and combinations thereof, or a wash-off product such as for example a hand dishwashing detergent, liquid hand soap, bar soap, body wash, shampoo, general purpose cleanser, and combinations thereof.

In one embodiment, the bioactive topical formulation includes a topically effective amount of the bioactive composition of the present invention. The bioactive topical formulation can further include a topically acceptable carrier. Suitable topically acceptable carriers can include, without limitation, a hydrophilic cream base, a hydrophilic lotion base, a hydrophilic surfactant base, a hydrophilic gel base, a hydrophilic solution base, a hydrophobic cream base, a hydrophobic lotion base, a hydrophobic surfactant base, a hydrophobic gel base, and/or a hydrophobic solution base. In one embodiment, the bioactive composition can be present in an amount ranging from between about 0.001 percent and about 99 percent of the total weight of the bioactive topical formulation.

Additional Uses for Ginseng (*Panax* Spp.) Bioactive Compositions (Serum Fractions) or Extracts In another embodiment, the Ginseng (*Panax* spp.) Bioactive Compositions (Serum Fractions or Extracts) can be used in functional beverages, functional food products, supplements, and formulations that include an effective amount of the bioactive composition of the present invention suitable for internal (oral) use. In another embodiment, the bioactive composition can be present in an amount ranging from between about 0.001 percent and about 99 percent of the total weight of the functional beverage, functional food product, and/or supplement.

Personal Care Uses Involving Ginseng (*Panax* Spp.) Bioactive Compositions (Serum Fractions) or Extracts Personal Care Composition:

The personal care compositions herein include a safe and effective amount of the bioactive composition of the present invention. The bioactive composition of the present invention may be in the form of a serum fraction, an extract, a powder, a juice, or a combination thereof.

The personal care compositions herein are intended for topical application to skin and/or hair, and are formulated accordingly (e.g., have suitable viscosity, color, fragrance, and feel properties). The present compositions may be cosmetic leave-on-type compositions such as moisturizing lotions and creams, or rinse-off-type compositions such as body washes, shampoos, hair conditioners, shower gels, skin cleansers, cleansing milks, shave prep compositions, and personal cleansing compositions. Rinse-off-type compositions are applied topically to the skin or hair and then subsequently removed (e.g., via washing and/or with an implement such as a towel or razor) within minutes of application. Some non-limiting examples of personal care compositions herein are cosmetic skin care compositions, makeup, hair care compositions, shave prep compositions, and personal cleansing compositions. The personal care compositions herein may be provided in a variety of forms, including, but not limited to, emulsions, lotions, milks, liquids, solids, creams, gels, mousses, ointments, pastes, serums, sticks, sprays, tonics, aerosols, foams, and/or pencils. In some instances, the present compositions may be in a form suitable for use with an implement such as, for example, a cosmetic applicator (powered or unpowered); a reusable or disposable wipe, tissue, towel, or diaper; a razor or other shaving device; a personal cleansing implement such as a mesh shower sponge, conventional sponge, or wash cloth; a swab; and/or a pen.

The compositions herein are generally prepared by incorporating an effective amount of the bioactive composition of the present invention into a dermatological carrier. The dermatological carrier should provide suitable properties for the particular topical application it is intended for. The bioactive composition of the present invention may be incorporated into the dermatological carrier using conventional methods such as are known in the art of making topical compositions. Such methods typically involve mixing of the bioactive composition of the present invention, dermatologically acceptable carrier, and other optional ingredients (when included) in one or more steps to a relatively uniform state, with or without heating, cooling, application of vacuum, and the like. Typically, emulsions are prepared by first mixing the aqueous phase materials separately from the fatty phase materials and then combining the two phases as appropriate to yield the desired continuous phase.

The compositions may be prepared to optimize stability (physical stability, chemical stability, photostability) and/or delivery of the active materials. This optimization may include appropriate pH (e.g., 7 or less), exclusion of materials that can complex with the active agent and thus negatively impact stability or delivery (e.g., exclusion of contaminating iron), use of approaches to prevent complex formation (e.g., appropriate dispersing agents or dual compartment packaging), use of appropriate photostability approaches (e.g., incorporation of sunscreen/sunblock, use of opaque packaging), etc. The personal care compositions herein may be made by incorporating the bioactive composition of the present invention into a dermatologically acceptable carrier using conventional techniques for making personal care compositions. The bioactive composition of the present invention may be obtained according to one or more of the techniques disclosed herein for making Ginseng serum fraction, Ginseng extract, Ginseng powder, and/or Ginseng juice. For example, a personal composition may be provided by obtaining an Ginseng serum fraction, which is optionally refined and stabilized, and incorporating the Ginseng serum fraction into a dermatologically acceptable carrier such as the carrier described in more detail below.

Dermatologically Acceptable Carrier:

The bioactive compositions of the present invention can be formulated as personal care compositions for use with various personal care applications. Such personal care compositions can include a dermatologically acceptable carrier at from 20% to 99.99% (e.g., from 50% to 99%, from 60% to 98%, from 70% to 95%, or even from 60% to 80%). The carrier may be aqueous or anhydrous. The form of the carrier is not particularly limited, and can be any suitable form known in the art for the application desired (e.g., solutions, dispersions, emulsions and combinations thereof). "Emulsions" refer to compositions having an aqueous phase and an oil phase. Emulsion carriers include, but are not limited to oil-in-water, water-in-oil and water-in-oil-in-water emulsions. Emulsion carriers herein may include from 0.01% to 10% (e.g., 0.1% to 5%) of an emulsifier (e.g., nonionic, anionic, cationic emulsifier, or a combination thereof). Suitable emulsifiers are disclosed in, for example, U.S. Pat. Nos. 3,755,560, 4,421,769, and *McCutcheon's Detergents and Emulsifiers*, North American Edition, pages 317-324 (1986).

Optional Ingredients:

The compositions of the present invention may contain a variety of optional ingredients that are conventionally used in the particular product type provided, as long as they do not unduly alter product stability, aesthetics or performance. The optional ingredients, when incorporated into the composition, should be suitable for use in contact with human keratinous tissue without undue toxicity, incompatibility, instability, allergic response, and the like within the scope of sound judgment. The *CTFA Cosmetic Ingredient Handbook*, Second Edition (1992) describes a wide variety of nonlimiting cosmetic and pharmaceutical ingredients. The compositions herein may from about 0.0001% to about 50%; from about 0.001% to about 20%; or, from about 0.01% to about 10%, by weight of the composition, of optional ingredients. Some non-limiting examples of optional ingredients include abrasives, absorbents, aesthetic components such as pigments, opacifying agents, colorings/colorants, particles, essential oils, anti-caking agents, foaming agents, antifoaming agents, binders, biological additives, vitamins, minerals, moisturizers, emollients, humectants, skin tone agents, lubricating agents, sensates (e.g., menthol), fragrances, antidandruff agents, buffering agents, bulking agents, chelating agents, chemical additives, biocides, denaturants, astringents, external analgesics, anti-inflammatory agents, sunscreen agents, film formers and/or polymers for aiding film-forming properties and substantivity of the composition, pH adjusters, propellants, reducing agents, sequestrants, conditioning agents, thickeners, and combinations of these. Some of these and other optional ingredients are described in more detail below.

The personal care compositions herein may include from about 0.1% to about 10% (e.g., from 0.5% to about 7%) of a conditioning agent to provide a particular conditioning benefit to hair and/or skin. For example, some suitable hair conditioning agents include silicones (e.g., silicone oils, cationic silicones, silicone gums, high refractive silicones, and silicone resins), organic conditioning oils (e.g., hydrocarbon oils, polyolefins, and fatty esters), and combinations thereof. Some non-limiting examples of suitable silicone conditioning agents, and optional suspending agents for the silicone, are described in U.S. Reissue Pat. No. 34,584; and U.S. Pat. Nos. 4,152,416, 4,364,837, 5,104,646, 5,106,609, 5,674,478, 5,750,122, 7,465,439, 7,041,767, and 7,217,777. Some non-limiting examples of skin conditioning agents include vitamins, minerals, peptides and peptide derivatives, sugar amines, sunscreens, oil control agents, particulates, flavonoid compounds, hair growth regulators, anti-oxidants and/or anti-oxidant precursors, preservatives, protease inhibitors, tyrosinase inhibitors, anti-inflammatory agents, moisturizing agents, exfoliating agents, skin lightening agents, sunless tanning agents, lubricants, anti-acne actives, anti-cellulite actives, chelating agents, anti-wrinkle actives, anti-atrophy actives, phytosterols and/or plant hormones, N-acyl amino acid compounds, antimicrobials, and antifungals. Other non-limiting examples of skin conditioning agents can be found in U.S. Pub. Nos. 2010/0272667 and 2008/0206373. In addition to providing a skin health and/or appearance benefit, skin conditioning agents for use in shave prep compositions may also help to reduce the coefficient of friction for the shave prep composition, thereby decreasing the potential for skin irritation related to shaving.

The personal care compositions herein may include from 0.05% to 5% (e.g., from 0.1% to 4% or even from 0.25% to 3%) of a thickening agent. Suitable classes of thickening agents include, but are not limited to carboxylic acid polymers, crosslinked polyacrylate polymers, polyacrylamide polymers, polysaccharides, gums and mixtures thereof. Non-limiting examples of suitable thickening agents are described in the *CTFA International Cosmetic Ingredient Dictionary*, $10^{th}$ Ed. (2004), pp. 2294-96.

The personal care composition herein may include from 5% to 50% of an anionic, zwitterionic, and/or amphoteric detersive surfactant. The concentration of the detersive surfactant in the composition should be sufficient to provide the desired cleaning and lather performance Some non-limiting examples of anionic detersive surfactants include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; dioctyl esters of sodium sulfosuccinic acid; and olefin sulfonates. Some particularly suitable examples of anionic surfactants are alkyl and alkyl ether sulfates. Other non-limiting examples of anionic detersive surfactants are described in U.S. Pat. Nos. 2,486,921; 2,486,922; 2,396,278; and 3,332,880.

The personal care compositions herein may include a cationic surfactant system that includes one or more cationic surfactants. If present, the cationic surfactant system may be incorporated into the composition at a level of from 0.1% to 10% (e.g., 0.5% to 8%, from 1% to 5%, or even from 1.4% to 4%). In certain hair care compositions, the cationic surfactant may be balanced to provide desirable ease-to-rinse, feel, rheology, and wet conditioning benefits.

The personal care compositions herein may include a high melting point fatty compound. The high melting point fatty compounds useful herein typically have a melting point of 25° C. or higher, and may be selected from the group consisting of fatty alcohols, fatty acids, fatty alcohol derivatives, fatty acid derivatives, and mixtures thereof. It is to be appreciated that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is to be appreciated that, depending on the number and position of double bonds, and length and position of the branches, certain compounds having certain required carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

The personal care compositions herein may include a cationic and/or a non-ionic polymer at an amount of from 0.05% to 3% (e.g., 0.075% to 2.0%, or even from 0.1% to 1.0%). Suitable cationic polymers will have cationic charge densities of at least 0.5 meq/gm (e.g., at least 0.9 meq/gm, 1.2 meq/gm, or even at least 1.5 meq/gm), but typically less than 7 meq/gm or even less than 5 meq/gm, at the pH of intended use of the composition, which may range from pH 3 to pH 9. Herein, "cationic charge density" of a polymer refers to the ratio of the number of positive charges on the polymer to the molecular weight of the polymer. The average molecular weight of such suitable cationic polymers will generally be between about 10,000 and 10 million, in one embodiment between about 50,000 and about 5 million, and in another embodiment between about 100,000 and about 3 million. Some non-limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, vinyl pyrrolidone, and cationic guar gum derivatives such as guar hydroxypropyltrimonium chloride. Some non-limiting examples of non-ionic polymers are polyalkylene glycols having a molecular weight of more than about 1000. Other non-limiting examples of polymers are disclosed in the CTFA Cosmetic Ingredient Dictionary, 3rd edition, edited by Estrin, Crosley, and Haynes, (The Cosmetic, Toiletry, and Fragrance Association, Inc., Washington, D.C. (1982)).

The personal care compositions herein may include a suspending agent at concentrations effective for suspending water-insoluble material in dispersed form in the compositions or for modifying the viscosity of the composition. Such concentrations range from about 0.1% to about 10%, preferably from about 0.3% to about 5.0%. Suspending agents useful herein include anionic polymers, nonionic polymers, and vinyl polymers.

The personal care compositions herein may include particles. The particles may be dispersed water-insoluble particles. The particles may be inorganic, synthetic, or semi-synthetic. The particles may have a mean average particle size of between 1 μm and 1 mm (e.g., between 10 μm and 800 μm, 50 μm and 500 μm, or even between 100 μm and 400 μm).

In some instances, the above cationic surfactants, together with high melting point fatty compounds and an aqueous carrier, may be combined to form a gel matrix in a hair care composition. A gel matrix may be suitable for providing certain hair conditioning benefits such as slippery feel during the application to wet hair and softness and moisturized feel on dry hair. In view of providing the above gel matrix, the cationic surfactant and the high melting point fatty compound are contained at a level such that the weight ratio of the cationic surfactant to the high melting point fatty compound is in the range of, preferably from about 1:1 to about 1:10, more preferably from about 1:1 to about 1:6.

Methods of Regulating Keratinous Tissue Condition

Personal care compositions comprising an effective amount of the bioactive composition of the present invention can be used to regulate a condition of mammalian keratinous tissue by topically applying the personal care composition to a portion of mammalian tissue in need of regulation. The present method may include identifying a target portion of skin and/or hair in need of treatment and/or where treatment is desired, and applying the personal care composition to the target portion of keratinous tissue. Identifying a target portion of keratinous tissue in need of treatment can be based on the presence of a visible condition (e.g., dryness, brittleness, split ends, undesirable feel, redness, inflammation, discoloration, or wrinkles). In some instances, the target portion of keratinous tissue may not exhibit visible signs of a condition, but a user may still wish to target such an area if it is one that is known to develop a condition (e.g., skin or hair surfaces that are typically not covered by clothing and areas of skin prone to shaving irritation).

Personal care compositions containing an effective amount of the bioactive composition of the present invention may be applied once a day, twice a day, or on a more frequent daily basis, during a treatment period. The treatment period is ideally of sufficient time for the bioactive composition of the present invention to provide the desired benefit. For example, the treatment period may be of sufficient time for the bioactive composition of the present invention to provide a noticeable and/or measurable improvement in a hair or skin condition. The treatment period may last for at least 1 week (e.g., about 2 weeks, 4 weeks, 8 weeks, or even 12 weeks). In some instances, the treatment period will extend over multiple months (i.e., 3-12 months) or multiple years. In some instances, a cosmetic composition containing an effective amount of bioactive composition of the present invention may be applied most days of the week (e.g., at least 4, 5 or 6 days a week), at least once a day or even twice a day during a treatment period of at least 2 weeks, 4 weeks, 8 weeks, or 12 weeks.

The personal care compositions herein may be applied locally or generally. In reference to application of the composition, the terms "localized", "local", or "locally" mean that the composition is delivered to the targeted area while minimizing delivery to keratinous surfaces where treatment is not desired. While certain embodiments herein contemplate applying a composition locally to an area, it will be appreciated that the compositions herein can be applied more generally or broadly to one or more keratinous surfaces. In certain embodiments, the compositions herein may be used as part of a multi-step beauty regimen, wherein the present composition may be applied before and/or after one or more other compositions.

Using the personal care compositions herein according to the present methods can provide a skin or hair benefit. Some non-limiting examples of skin benefits include reducing the appearance of wrinkles, deep lines, fine lines, crevices, bumps, large pores; increasing the convolution of the dermal-epidermal border; skin lightening; increasing elasticity, decreasing sagging, reducing cellulite; reducing the appearance of under-eye circles, reducing the appearance of discoloration, reducing hyperpigmentation, increasing skin luminosity, and combinations thereof. Some non-limiting examples of hair benefits include shine, softness, combability, antistatic properties, wet-handling, damage, anti-dandruff, manageability, body, and greasiness.

The personal care compositions may be applied by any suitable means known for applying such products, including rubbing, wiping or dabbing with hands, fingers and/or an implement. Non-limiting examples of implements include a sponge or sponge-tipped applicator, a swab (for example, a cotton-tipped swab), a pen optionally comprising a foam or sponge applicator, a brush, a wipe, and combinations thereof. The composition may be pre-applied to the applicator and, for example, delivered to the user pre-packaged as such, or the user may be instructed to apply the composition to the applicator prior to use. In some instances, the composition may be stored in an implement, for example, in a separate storage area for the composition. In this example, the composition may be transferred to the applicator from the storage area, for example, by squeezing and/or breaking or by other suitable means. The composition may be applied to the keratinous tissue by contacting the applicator and composition to the skin. Contact may include, for example, light pressure, dabbing, rubbing, wiping, or any other suitable means. When targeted application is desired, the composition may be applied to the desired area of keratinous tissue.

EXAMPLES

The present invention is now described with reference to the following Examples. These Examples are provided for the purpose of illustration only and the invention should in no way be construed as being limited to these Examples, but rather should be construed to encompass any and all variations which become evident as a result of the teaching provided herein. Thus, the following examples are intended to illustrate particular embodiments of the present invention, but are by no means intended to limit the scope of the present invention.

Example 1

Preparation of Bioactive Composition from Ginseng (*Panax quinquefolius* L.)

Ginseng plants were cultivated over four growing seasons. Whole mature cultivated Ginseng plants were dug from the soil when they reached the phase of growth with ripe fruit (berries). Collected whole plants were immediately cleaned with water. Viability of the collected plants was tested utilizing an OS5p multi-mode chlorophyll fluorometer (Opti-Sciences Inc, Hudson, N.H., USA). After maceration and pressing of whole live Ginseng plants the yield of Fraction A (Press-Cake) was between 35% and 55% (w/w) and intracellular dispersion contained from 8% to 12% dry matter. "Adjustment 1" was achieved by titration of intracellular dispersion with, e.g., acid to pH=3.0. The dispersion was immediately subjected to destabilizing treatment by electromagnetic waves in a continuous flow system that includes magnetrons. The parameters of said electromagnetic waves in destabilization step of the invention were set to achieve the decrease in the value of real component of low-frequency dielectric constant ($\varepsilon'_0$) of intracellular dispersion during the treatment by about 10 Farads per meter (F/m)—compared to its value prior to treatment (from 80 F/m to 70 F/m). "Adjustment 2" was achieved by increase of pH level in "Supernatant 1" by titration with alkali to pH=8.0. As used herein and in the process illustrated in FIG. 2, "Separation 2" was achieved by mechanical separation of adjusted Supernatant 1 to produce "Supernatant 2" and "Fraction C (Precipitate 2)". As used herein and in the process illustrated in FIG. 2, "Adjustment 3" was achieved by decrease of pH level in "Supernatant 2" by titration with acid to pH about 3.5. As used herein and in the process illustrated in FIG. 2, "Adjusted Supernatant 2" refers to Fraction D (Serum Fraction), a material obtained after "Adjustment 3" and mixed with "Preservatives and Stabilizers". It was unexpectedly found that the biological constituents remaining in serum and subsequently in the finished ingredient are substantially free from pulegone and protein.

Example 2

Preparation of Bioactive Composition from Ginseng (*Panax quinquefolius* L.)

Ginseng plants were cultivated over four growing seasons. Whole mature cultivated Ginseng plants were dug from the soil when they reached the phase of growth with ripe fruit (berries). Collected whole plants were immediately cleaned with water. Viability of the collected plants was tested utilizing an OS5p multi-mode chlorophyll fluorometer (Opti-Sciences Inc, Hudson, N.H., USA). After maceration and pressing of whole live Ginseng plants the yield of Fraction A (Press-Cake) was between 35% and 55% (w/w) and intracellular dispersion contained from 8% to 12% dry matter. "Adjustment 1" was achieved by titration of intracellular dispersion with, e.g., acid to pH=3.0. The dispersion was immediately subjected to destabilizing treatment by electromagnetic waves in a continuous flow system that includes magnetrons. The parameters of said electromagnetic waves in destabilization step of the invention were set to achieve the decrease in the value of real component of low-frequency dielectric constant ($\varepsilon'_0$) of intracellular dispersion during the treatment by about 30 Farads per meter (F/m)—compared to its value prior to treatment (from 80 F/m to 50 F/m). "Adjustment 2" was achieved by increase of pH level in "Supernatant 1" by titration with alkali to pH=8.0. As used herein and in the process illustrated in FIG. 2, "Separation 2" was achieved by mechanical separation of adjusted Supernatant 1 to produce "Supernatant 2" and "Fraction C (Precipitate 2)". As used herein and in the process illustrated in FIG. 2, "Adjustment 3" was achieved by decrease of pH level in "Supernatant 2" by titration with acid to pH about 3.5. As used herein and in the process illustrated in FIG. 2, "Adjusted Supernatant 2" refers to Fraction D (Serum Fraction), a material obtained after "Adjustment 3" and mixed with "Preservatives and Stabilizers". It was unexpectedly found that the biological constituents remaining in serum and subsequently in the finished ingredients are substantially free from pulegone and protein.

Example 3

Methods for Determining Effects of Bioactive Compositions

Processes of irritation and inflammation in human skin are often undesirable and can cause lasting cumulative damage which includes visible signs of skin aging (e.g. discoloration and wrinkles), decreased mechanical strength, decreased protective functions, and lessened ability to recover from stress and injuries. These processes can be caused by a variety of stresses and insults to the skin. Especially ubiquitous stresses are sunlight and surfactants. Mitigating irritation and inflammation of the skin, particularly those caused by common stresses, is important and desirable.

Adverse effects of light, most commonly sunlight (though artificial sources are included), on human skin are well known. Overly high exposure to sunlight may cause acute adverse reaction involving irritation and inflammation, such as sunburn. Exposures insufficient to cause acute reactions can still trigger inflammation-related processes. Accumulated inflammatory damage from sunlight exposure causes degradation of skin resilience and development of undesirable appearance, in a process known as photoaging.

Surfactants are used in a variety of personal care and cleansing products to allow or improve processes of cleansing, foaming, emulsifying, solubilizing, and dispersing. Repetitive contact with surfactant-containing products has been shown to cause damage of the skin barrier due to surface or interface activities of the surfactants [Walters R M, Mao G, Gunn E T et al. Cleansing formulations that respect skin barrier integrity. Dermatol Res Pract 2012; 495917: 1-9]. The weakened barrier subsequently leads to deeper penetration of the surfactants into skin and induced irritation and inflammation [De Jongh C M, Jakasa I, Verberk M M, Kezic S. Variation in barrier impairment and inflammation of human skin as determined by sodium lauryl sulphate penetration. Br J Dermatol 2006; 154 (4): 651-7. Ananthapadmanabhan K P, Yang L, Vincent C et al. A novel technology in mild and moisturizing cleansing liquids. Cosmetic Dermatology® 2009; 22 (6): 307-16], which can be perceived by consumers as dryness, itchiness, swelling, redness, and pain. As surfactants are widely used in hand soaps, facial and body washes, shampoos and conditioners, as well as dish, laundry and housecleaning detergents, human skin contact with surfactants is frequent.

Irritation and inflammation are commonly viewed as a "cascade" proceeding from necessary release of a signaling compound Interleukin (IL) 1-alpha (or IL-1a) to induction of other downstream cytokines and chemokines such as interleukins IL-6 and IL-8 or other signaling molecules [Welss T, Basketter D A, Schroder K R. In vitro skin irritation: facts and future. State of the art review of mechanisms and models. Toxicol In Vitro 2004; 18 (3): 231-43]. However, previously published data suggest that "cascade" view might not be a comprehensive model [Koganov, M., Zhang, L., Duev, A., Dueva-Koganov, O., Hou, X., Biological Activities of Novel Ingredients from Living Tea Plant (*Camellia sinensis*), Household and Personal Care Today, 9 (2015) 19-24; and Koganov M, Zhang L, Duev A. Imparting mildness with living tea plant ingredient. Personal Care, 2013; 14(5): 31-4].

Even Sodium Dodecyl Sulfate (SDS), a single compound commonly used as benchmark source of surfactant stress in both in vitro and in vivo studies, can trigger different portions of the irritation and inflammation process without significantly affecting release of a primary cytokine such as IL-1α, depending on concentration. The complexity of irritation and inflammation response of skin cells implies that signaling "network" model is a more adequate analogy than a signaling "cascade" model. This indicates that mitigation of such a complex signaling process must affect more than one pathway, such as by using a multifunctional bioactive ingredient.

One of the methodologies for studying and quantifying irritation and inflammation includes culturing cells of the tissue most likely to come in contact with stress sources, such as viable epidermal keratinocytes from human skin. Human epidermal keratinocytes (HEK) have become the focus of attention in irritant-induced skin inflammation by virtue of their epidermal location, importance in maintaining the integrity of the stratum corneum barrier, and the ability to produce a variety of inflammatory mediators [Weiss T, Basketter D A, Schroder K R. In vitro skin irritation: facts and future. State of the art review of mechanisms and models. Toxicol In Vitro 2004; 18 (3): 231-43]. Keratinocytes can release numerous signalling substances such as interleukins in response to a range of irritants including surfactants and sunlight. Amounts of these mediators can then be measured via techniques such as Enzyme-Linked Immunosorbent Assay (ELISA). Bioactive substances capable of reducing HEK release of these inflammatory mediators may help control the signs of irritation and inflammation in human skin.

In addition to interleukins, arachidonic acid metabolites are long known to have significant roles in inflammatory processes. Prostaglandin E2 (PGE2) is one of the most abundant metabolites of arachidonic acid, generated through an enzymatic cascade controlled by cyclooxygenase (COX) enzymes. The importance of PGE2 in inflammation signaling is highlighted by the wide clinical use of COX inhibitors (including those initially of plant origin, such as aspirin) to relieve inflammation.

The tests selected for determining effects of ingredients of present invention include inhibition of chemokines, cytokines and prostaglandins (signalling compounds) in cultured human skin cells, inhibition of a compound capable of both signalling and causing damage in cultured human cells, and measuring release or lack thereof of substances indicating cell damage or sensitization. The cells used were normal human adult epidermal keratinocytes (HEK). Those knowledgeable in above areas and related conditions as well as other specialties may find other methods of practicing the invention. However, those methods are deemed to be within the scope of this invention.

The following examples illustrate, but do not serve to limit the scope of the invention described herein. They are meant only to suggest a method of practicing the invention. The selection of the in vitro bioassays was based on following rationale: to assure test articles safety by demonstrating the lack of cytotoxicity and sensitization potential; and to determine their efficacy and potency in inhibiting signalling and damaging compounds involved in skin irritation, inflammation and aging processes, for example those induced by various stresses. Stress sources may include important and ubiquitous factors such as sunlight and surfactants.

Example 4

Evaluation of Cytotoxicity (Assessment of Safety)

Lactate Dehydrogenase (LDH) is a key cytoplasmic enzyme. Presence of LDH outside the cells at levels above normal background leakage is an indicator of cell damage or cell death. Assay quantifying LDH in cell culture medium is often employed to assess potential cytotoxicity of test articles and stress factors. Observation of cells under microscope to note cell rupture or changes in cell morphology can also contribute to assessment of cytotoxicity.

Normal human adult epidermal keratinocytes (HEK) and all cell culture supplies were obtained from Life Technologies Co. (Carlsbad, Calif., USA). The cells were grown and then maintained in keratinocyte basal medium 154 (M154) with added human keratinocyte growth supplements (HKGS) at 37° C. in an atmosphere of 5% $CO_2$ and used between passages 2 to 4. For the experiments, HEK cells were trypsinized, seeded in 96-well plates, and grown to ~80% confluence. HEK were then exposed, or not, to a stress factor, and incubated for 16 hours with or without test articles at various concentrations. After incubation, HEK cell supernatant medium samples were collected, and levels of LDH were evaluated using Cytoscan™ LDH Assay kit (Catalog #786-210, produced by G-Biosciences, St. Louis, Mo., USA). Untreated, unstressed HEK cells were lysed using kit-supplied lysis buffer as a positive control, with lysate used as assay positive control and a measure of maximum LDH release. Lower induced LDH release, when confirmed by microscopy, indicates lower cytotoxicity.

Example 5

Evaluation of Skin Sensitization Potential (Assessment of Safety)

It is possible for a test article to not be cytotoxic, and yet be unsafe due to provoking an allergic reaction upon skin contact. Typically, initial exposure to an allergen sensitizes the immune system, and following exposures cause an allergic response. Recent progress in understanding the mechanisms of skin sensitization identified interleukin-18 (IL-18) production in normal human epidermal keratinocytes (HEK) as a useful biomarker for skin contact sensitization [Corsini E, Mitjans M, Galbiati V, Lucchi L, Galli C L, Marinovich M, Use of IL-18 production in a human keratinocyte cell line to discriminate contact sensitizers from irritants and low molecular weight respiratory allergens. Toxicol In Vitro. 2009 August; 23(5):789-96]; [Teunis M, Corsini E, Smits M, Madsen C B, Eltze T, Ezendam J, Galbiati V, Gremmer E, Krul C, Landin A, Landsiedel R, Pieters R, Rasmussen T F, Reinders J, Roggen E, Spiekstra S, Gibbs S, Transfer of a two-tiered keratinocyte assay: IL-18 production by NCTC2544 to determine the skin sensitizing capacity and epidermal equivalent assay to determine sensitizer potency. Toxicol In Vitro. 2013 April; 27(3): 1135-50]. IL-18 is considered a suitable in vitro alternative to animal skin sensitization testing methods such as Local Lymph Node Assay. We therefore evaluated IL-18 production in HEK treated with test articles to determine their sensitization potential.

Normal human adult epidermal keratinocytes (HEK) were cultured as described in Example 4 above. After incubation with test articles or controls for 16 hours, the HEK cells were lysed with 100 μl/well of 0.5% Triton X-100 in pH 7.4 Phosphate Buffered Saline (PBS). The cell lysates were collected, and IL-18 was quantified using Human IL-18 ELISA Kit (Catalog #7620, produced by MBL International Co., Woburn, Mass., USA). A known skin sensitizer, paraphenylenediamine (pPD) used as a positive control, significantly induced IL-18 compared to vehicle control in HEK cultures. Fold changes of IL-18 levels between test articles and respective vehicle controls were calculated and compared to pPD (positive control). Lower induction of IL-18 indicates lower sensitization potential.

Example 6

Inhibition of IL-8 Induced by SDS (Assessment of Potency and Efficacy Against Surfactant-Induced Irritation/Inflammation Signaling Substances)

Normal human adult epidermal keratinocytes (HEK) were cultured as described in Example 4. The cells were then incubated with test articles and/or controls for 16 hours.

Presence of Sodium Dodecyl Sulfate (SDS) in cell cultivation medium at specific concentrations was used for induction of chemokines and cytokines. IL-8 was induced by 6 μg/mL SDS. After incubation, HEK cell supernatants were collected. Quantikine® ELISA kits (R&D Systems Inc, Minneapolis, Minn.) were used to quantify these interleukins in the supernatants. IL-8 was quantified by Human CXCL/IL-8 Immunoassay kit (Catalog #D8000C). $IC_{50}$ (concentration of test article necessary to reduce interleukin levels to 50%, with samples from untreated cells considered as 0% and samples treated solely with respective inducing quantity of SDS as 100%) values were calculated by sigmoidal curve fitting with SigmaPlot 10.0 (Systat Software). Lower $IC_{50}$ values indicate higher potency and a degree of efficacy.

Example 7

Inhibition of IL-6 and/or IL-8 and/or PGE2 Induced by Full-Spectrum Sunlight from Artificial Source (Assessment of Potency and Efficacy Against Sunlight-Induced Irritation/Inflammation Signaling Substances)

Normal human adult epidermal keratinocytes (HEK) were cultured as described in Example 4. The cells were washed once, and M154 was replaced with PBS. Both the washing and the replacement were done with PBS, to remove light-absorbing components of M154. The 96-well plate containing HEK was then covered with UV-transparent 1 mm quartz sheet, placed on white underlay atop controlled Peltier-cooled surface maintaining room temperature, and irradiated with a dose of 20 $J/cm^2$ of artificially produced full spectrum sunlight at dose rate of about 1100 $W/m^2$, as measured via pyranometer through same quartz cover. PBS was then removed and replaced with M154, and cells were incubated with test articles and/or controls for 16 hours. Identical manipulations, with exception of presence of sunlight, were carried out with HEK serving as unstressed controls. Irradiation equipment was obtained from Solar Light Company, Glenside, Pa. and included Solar Simulator LS1000-6R-002 in Airmass 1.5 configuration using plain mirror; XPS1000 precision current source, and PMA2144 Pyranometer. After incubation, HEK cell supernatants were collected. Quantikine® ELISA kits (R&D Systems Inc, Minneapolis, Minn.) were used to quantify interleukins in the supernatants. IL-8 was quantified by Human CXCL/IL-8 Immunoassay kit (Catalog #D8000C), IL-6 was quantified by Human IL-6 Immunoassay kit (Catalog #D6050); and PGE2 was quantified using Parameter™ Prostaglandin $E_2$ Assay (Catalog #KGE004B). $IC_{50}$ (concentration of test article necessary to reduce interleukin or prostaglandin levels to 50%, with samples from non-irradiated cells considered as 0% and from irradiated cells considered as 100%) values were calculated by sigmoidal curve fitting with SigmaPlot 10.0 (Systat Software). Lower $IC_{50}$ values indicate higher potency and a degree of efficacy.

Example 8

Physico-Chemical Characteristics of Processing Samples and Bioactive Compositions: Methods of Evaluation Various methods were used to evaluate the physico-chemical characteristics of interim processing samples, and bioactive compositions produced according to embodiments of the process of the present invention.

The test methods are described in Table 1, below.

TABLE 1

| Physico-Chemical Methods of Evaluation | | |
|---|---|---|
| Property | Test Method | Units |
| Appearance | Determined organoleptically. | N/A |
| Odor | Determined organoleptically. | N/A |
| Color | Determined on Lovibond Comparator 3000 Gardner Scale. Turn on comparator lamp. Measure 8 mL of sample into sample tube. Insert tube into comparator. Rotate the knobs until two color standards nearest in color to the sample have been located. Record the value of the sample color accordingly. If the color of the sample is substantially similar to both, rather than a single standard, then record it as a value between the values of the two standards. | Gardner scale |
| Dry Matter | Dry matter is determined by comparing the weights of liquid sample with residual dry matter after water has been evaporated. Procedure is based on standard laboratory practices commensurate with available equipment. Take three disposable aluminum weighing dishes (VWR 25433-016) and distinctly number them with a permanent marker on the outside. Allow marker ink to dry. Turn on the Ohaus Explorer E00640 balance (Ohaus Corporation) and allow it to start up. Zero the weight. Place a dish on the balance and record the weight for that dish as 'tare'. Without removing the dish from the balance, add approximately 4 mL of liquid sample and record the weight for that dish as 'tare + wet'. Set the dish with sample aside. Repeat the above with two remaining dishes. Leave the dishes for 24 hours in the ThermoScientific "Lindberg Blue M" Gravity oven at 105 degrees Celsius. Remove the dishes and allow them to cool for approximately 5 minutes at room temperature. Weigh each dish with dried residue individually and record the weight as 'tare + dry'. Dry matter percentage is calculated as ('tare + dry' − 'tare')/('tare + wet' − 'tare') * 100. Record dry matter percentage for the sample as mean of dry matter percentage for the three dishes. | % |
| Refractive index | Determined by measuring on Reichert Arias 500 refractometer with temperature regulation provided by Cole-Parmer Polystat temperature controller, model number 12108-10. Procedure is based on the instruction manual for Arias 500 refractometer, sections 6.0, 4.1 and 4.4-4.5. Turn on the temperature controller, set temperature to 20 degrees Celsius. Turn on refractometer. Ensure that Automatic Reading Method is enabled. Deposit approximately 0.5 mL of deionized water on the surface of the lower measuring prism. Close the cell, taking care to avoid bubble formation. Turn shadowline adjustment knob to bring the shadowline within the crosshairs. Wait for temperature at refractometer measuring cell to completely stabilize, then push Read button. Retry above steps until refractive index of deionized water is determined as 1.333 at least three times in a row. Rinse the lower and upper surfaces of the measuring cell with deionized water and blot dry with lint-free wipe. Deposit approximately 0.5 mL of sample on the surface of the lower measuring prism. Close the cell and turn the shadowline adjustment knob to bring the shadowline within the crosshairs. Wait for temperature at refractometer measuring cell to completely stabilize, then push Read button and note the reading. Rinse the lower and upper surfaces of the measuring cell with deionized water and blot dry with lint-free wipe. Repeat above steps until stable readings have been obtained for sample material at least three times in a row. Record the value of these stable readings as refractive index of the sample material. | nD |

TABLE 1-continued

Physico-Chemical Methods of Evaluation

| Property | Test Method | Units |
|---|---|---|
| Density | Determined with Densito 30PX densitometer from Mettler Toledo. Procedure is based on Operating Instructions for Densito 30PX, sections 4 and 6. Push and hold the power button on the densitometer for a second to turn it on. Once the instrument starts up, ensure that the display is set to g/cm3 units. Depress the plunger button fully, submerge the sampling tube in deionized water and slowly push the fill trigger to fill the sample loops with 4 cm3 of deionized water. Avoid bubble intake or formation. Note the reading. If it deviates by more than 0.05% from expected density of water at the ambient temperature, recalibrate the densitometer as per Operating Instructions. After ensuring that the unit display and calibration for densitometer are proper, eject the water into a waste receptacle by depressing the plunger button fully. Submerge the sampling tube in liquid sample and push the fill trigger to fill the sample loops with 4 cm3 of sample. Avoid bubble intake or formation. Note the reading once it stabilizes. Eject the sample from densitometer into a waste receptacle and repeat steps above for additional readings, until receiving three matching readings in a row. Record that as the value of density (specific gravity) for the sample. | $g/cm^3$ |
| pH | Determined by measuring on a pH meter such as Denver Instrument Model 250 pH/ISE/conductivity meter with pH/ATC electrode number 300729.1. Procedure is based on Denver Instrument Company 301127.1 Rev. D manual, pages ii and 9 through 12. The pH 4.01 and pH 7.00 buffers used to calibrate the pH meter during the product specification determination were acquired from Thermo Electron Company. | N/A |
| Total Plate Count | Determined as per US Pharmacopoeia XXX, NF25, <61>, Microbiological Limit Tests | CFU/gm |
| Mold/Yeast | Determined as per US Pharmacopoeia XXX, NF25, <61>, Microbiological Limit Tests | CFU/gm |
| *E. coli* | Determined as per US Pharmacopoeia XXX, NF25, <61>, Microbiological Limit Tests | CFU/gm |
| *Salmonella* sp. | Determined as per US Pharmacopoeia XXX, NF25, <61>, Microbiological Limit Tests | CFU/gm |
| *Staphylococcus aureus* | Determined as per US Pharmacopoeia XXX, NF25, <61>, Microbiological Limit Tests | CFU/gm |
| *Pseudomonas* sp. | Determined as per US Pharmacopoeia XXX, NF25, <61>, Microbiological Limit Tests | CFU/gm |
| Pulegone | Determined per [Corrado L. et al. Quantitative analysis of α, β-thujone, pulegone, safrole, coumarin and β-asarone in alcoholic beverages by selected-ion monitoring. Journal of Applied Toxicology. Volume 4, Issue 5, pages 273-276, October 1984] | ppm |
| Protein | According to: Kjeldahl; Hitachi L-8900 amino acid analyzer | % |
| Color characteristics | L*a*b* values of Ginseng (*Panax quinquefolius*) processing samples (from the process described in Example 1) were measured using Konica Minolta CM-2600d spectrophotometer, as follows: Intracellular dispersion, Supernatant 1 and Supernatant 2 were measured after combining and mixing with ultrapure distilled water - via transflection in cuvette, using 8 mm aperture; Fraction B and C were packed in cut-off vial over microscope slide cover slip. Calibration 1 was conducted as follows: Black - black plastic provided with CM-A145 standard; White: white backstop of cell holder through cuvette with ultrapure distilled water. Calibration 2 was conducted as follows: Black - black plastic provided with CM-A145 standard; White: CM-A145 standard covered with VWR 48366 045 microscope slide cover slip. | L*a*b* |
| FT-IR transmission spectra | Samples from the process described in Example 1 were dried for 16 hours at 105 deg. C.; dry residue was grinded, then pressed with digital pressure clamp (force readout 20 units) to ZnSe ATR crystal of Pike MIRacle ATR attachment of PerkinElmer Spectrum 100 FT-IR spectrometer. FT-IR transmission spectra in the range of wavenumbers between 4000 $cm^{-1}$ and 700 $cm^{-1}$ were then taken, and the data subjected to baseline adjustment, smoothing, and noise removal (collectively performed by "Data Tune-Up" procedure in FT-IR software). | FT-IR spectra |

TABLE 1-continued

Physico-Chemical Methods of Evaluation

| Property | Test Method | Units |
|---|---|---|
| Ginsenoside Analysis | LC-MS approach was used to simultaneously analyze Ginsenosides: Rh1, Rh2, Rg1, Rg2 and Rg3. Sample Preparation: 5 mg of each Ginsenoside standard was dissolved in 1 ml 15% water/85% methanol as stock solutions. They were further diluted 10, 100, 1000 times in 30% water/70% methanol. Standard solutions were stored at −4 C. in the freezer. Samples were either injected neat or diluted 40 times in 30% water/70% methanol. Ginsenosides analysis: Column. 10 cm × 4.6 mm × 2.6 μm 100 A, Kinetex C18 Coreshell (Temperature = 40 C.). Injection: 5 μl for all samples; 5 ul or 2 ul for standards. All samples are under 4 C in autosampler. Solvents: solvent A (100% Water with 0.1% Formic acid) and solvent B (100% Acetonitrile with 0.1% Formic acid), flow rate 0.8 ml/min. Detector: Split between DAD and MS. MS ESI+ 50-1500 and ESI− 50-1500; 45 min. | ppm |

Example 9

Physico-Chemical and Analytical Characteristics of Processing Samples and Bioactive Compositions Color characteristics of Ginseng (*Panax quinquefolius*) interim processing samples (from the process described in Example 1) are presented in Table 2 below.

TABLE 2

Color Characteristics of Ginseng (*Panax quinquefolius*) Processing Samples (From the Process Described in Example 1)

| Processing Sample | SCI/ SCE | Color Characteristics | | | |
|---|---|---|---|---|---|
| | | L* (D65) | a* (D65) | b* (D65) | Calibration |
| Intracellular dispersion | SCI | 37.19 | −12.73 | 45.85 | 1 |
| Supernatant 1 | SCI | 63.55 | 32.35 | 89.15 | 1 |
| Precipitate 1 (Fraction B) | SCE | 27.05 | 3.23 | 28.23 | 2 |
| Adjusted Supernatant 2 | SCI | 64.57 | 24.38 | 88.57 | 1 |
| Precipitate 2 (Fraction C) | SCE | 12.18 | −0.87 | 5.15 | 2 |

Physico-Chemical Characteristics of Ginseng (*Panax quinquefolius*) interim processing samples (from the process described in Example 1) are presented in Table 3 and FIG. 3 below.

TABLE 3

Physico-Chemical Characteristics of Ginseng (*Panax quinquefolius*) Processing Samples (From the Process Described in Example 1)

| Parameter | Processing Sample | | | |
|---|---|---|---|---|
| | Intracellular Dispersion | Supernatant 1 | Supernatant 2 | Adjusted Supernatant 2 |
| Dry matter, % | 10.49 | 7.12 | 7.35 | 7.47 |
| NMR τ$_2$, ms | 84.2 | 95.6 | 570.1 | 361.7 |
| pH | 5.43 | 2.93 | 7.59 | 3.50 |
| Turbidity, NTU | >9999 | 33 | 13 | 18 |

Figure 3:
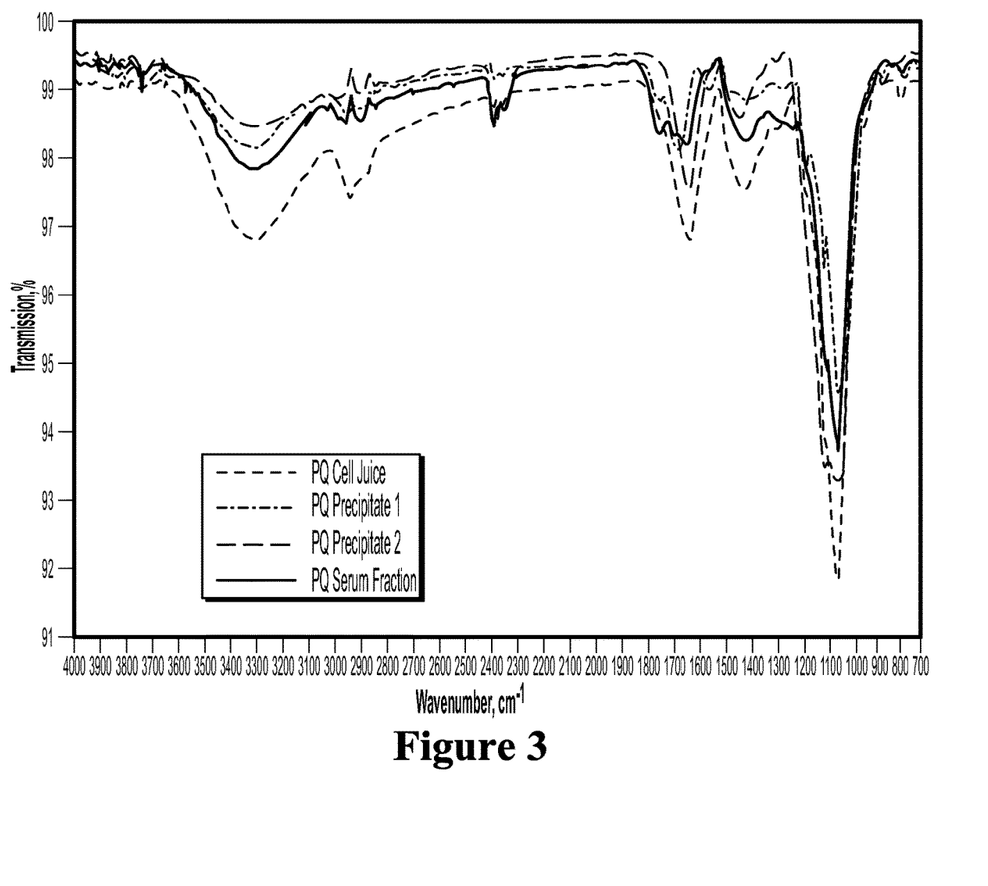
FIG. 3 is a graph showing FT-IR transmission spectra of Ginseng (*Panax quinquefolius*) samples process in accordance with one embodiment of the present invention. The embodiment of the process used to produce the samples shown in FIG. 3 is described in Example 1.

FT-IR transmission spectra of Ginseng (*Panax quinquefolius*) processing samples (from the process described in Example 1) is presented in FIG. 3

Bioactive compositions were prepared according to the process described in Examples 1 and 2. Results of their physico-chemical and analytical evaluations are shown in Table 4 below.

TABLE 4

Results of Physico-Chemical and Analytical Evaluations of Bioactive Compositions Prepared According to Examples 1 and 2

| Characteristics | Bioactive Compositions | |
|---|---|---|
| | Example 1 | Example 2 |
| Appearance | Yellow Liquid | Yellow Liquid |
| Odor | Characteristic | Characteristic |
| Solubility in water | Soluble in any ratio | Soluble in any ratio |
| Color (Gardner scale) | 10.5 | 10.5 |
| Dry matter (%) | 8.0 | 8.28 |
| Refractive index (nD) | 1.348 | 1.348 |
| pH | 3.9 | 3.8 |
| Total Plate Count (CFU/g) | <10 | <10 |
| Mold/Yeast (CFU/g) | <10 | <10 |
| *E. coli* (CFU/g) | Negative/10 g | Negative/10 g |
| *Salmonella* sp. (CFU/g) | Negative/10 g | Negative/10 g |
| *Staphylococcus aureus* (CFU/g) | Negative/10 g | Negative/10 g |
| *Pseudomonas* sp. (CFU/g) | Negative/10 g | Negative/10 g |
| Ginsenoside Rh1 | 9.4 | 29 |
| Ginsenoside Rh2 | 6.2 | 69 |
| Ginsenoside Rg1 | 580 | 470 |
| Ginsenoside Rg2 | 60 | 320 |
| Ginsenoside Rg3 | 3.5 | 15 |
| Sum of five Ginsenosides (Rh1, Rh2, Rg1, Rg2, Rg3) | 660 | 900 |
| Protein | less than 0.500% | less than 0.675% |
| Pulegone | less than 25 ppm | less than 25 ppm |

Example 10

Biological Activities of Bioactive Composition from Ginseng (*Panax quinquefolius*)

Bioactive Composition from Ginseng (*Panax quinquefolius*) were prepared according to an embodiment of the process of the present invention and tested for certain biological activities.

Table 5 includes safety and activity data of bioactive composition from ginseng (*Panax quinquefolius*) obtained in the following tests: cytotoxicity (LDH/microscopy), sensitization potential (IL18), full spectrum sun induction of IL8; IL6 and PGE2; SDS induction of IL8.

TABLE 5

Safety and Biological Activity Results

| Assay | Example 1 | Example 2 |
|---|---|---|
| HEK Cytotoxicity (LDH/microscopy) | No cytotoxicity at concentrations up to 0.5% v/v, which do not cause notable LDH release in Human Epidermal Keratinocyte monolayer culture. This suggests lack of cytotoxicity in human skin. | No cytotoxicity at concentrations up to 0.5% v/v, which do not cause notable LDH release in Human Epidermal Keratinocyte monolayer culture. This suggests lack of cytotoxicity in human skin. |
| HEK IL18 (sensitization) | Not a notable sensitizer | Not a notable sensitizer |
| HEK IL8/SDS | $IC_{50} \approx 0.2\%$. Higher concentrations induce. | Max inhibition 38% at 0.08%. Higher concentrations induce. |
| HEK $PGE_2$/Sun | Notable inhibition between 0.001% and 0.1%. Induction at $\geq 0.2\%$ | No notable inhibition. Induction at $\geq 0.1\%$ |
| HEK IL6/Sun | Max inhibition $\approx$ 40%-43% at 0.05%-0.1%. Induces at $\geq 0.1\%$ | No notable inhibition. Induces at $>0.05\%$ |
| HEK IL8/Sun | Max inhibition 33% at 0.1%. Higher concentrations induce. | No notable inhibition. Dose-dependent induction. |

In summary, biological activity results showed that bioactive compositions of ginseng (*Panax* spp.): (i) are not potential skin sensitizers according to in vitro test; (ii) are not cytotoxic in vitro at selected concentrations that could be relevant to their concentrations in finished product formulation; and (iii) show in vitro activities indicating potential usefulness for mitigating signs of skin aging caused by inflammation and related process (e.g., those triggered by stresses to the skin, including environmental stress such as full-spectrum sun exposure or surfactant-induced stress).

It is unexpected and surprising discovery that while Bioactive Composition prepared according to Example 2 has higher individual concentrations of most of the ginsenosides analyzed and higher total ginsenoside concentration than Bioactive Composition prepared according to Example 1, its biological activities are lower or absent. Especially notable is the difference at inhibiting sunlight-induced $PGE_2$.

Example 11

Preservative and Stabilizer System for the Bioactive Compositions from Ginseng (*Panax* Spp.)

Various preservatives and stabilizers were tested for use with the bioactive serum fractions and bioactive extracts of the present invention. Provided below in Table 6 is one example of a combination/concentrations of preservatives and stabilizers that was used for preparing bioactive compositions (e.g., those described in Examples 1 and 2).

TABLE 6

Combination and Concentrations of Preservatives and Stabilizers Used for Bioactive Compositions Described in Examples 1 and 2

| Preservative/Stabilizer | Amount (wt %) |
|---|---|
| Pentylene Glycol (CAS 5343-92-0) | 1.90% |
| Tetrasodium EDTA (CAS 64-02-8) | 0.25% |
| Sodium metabisulfite (CAS 7681-57-4) | 0.20% |
| Potassium sorbate (CAS 590-00-1) | 0.10% |
| Sodium Benzoate (CAS 532-32-1) | 0.10% |
| Bioactive Serum Fraction or Extract | 97.45% |

While the preservatives and stabilizers provided above were found to be effective, other preservatives and stabilizers that are known in the art could also be as affective with the bioactive serum fractions and bioactive extracts of the present invention. The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

As used in the description and the appended claims, the singular forms "a," "an," and "the" are intended to include the plural forms as well, unless the context clearly indicates otherwise. All percentages disclosed herein are by weight of the total composition, unless specifically stated otherwise. All ratios are weight ratios, unless specifically stated otherwise. The number of significant digits conveys neither a limitation on the indicated amounts nor on the accuracy of the measurements. All numerical amounts are understood to be modified by the word "about" unless otherwise specifically indicated. All measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified. All numeric ranges are inclusive of narrower ranges and combinable; delineated upper and lower range limits are interchangeable to create further ranges not explicitly delineated.

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A bioactive serum fraction derived from a ginseng (*Panax* spp.) plant, wherein said bioactive serum fraction comprises:
   (i) a total pulegone content of less than 100 ppm,
   (ii) a total protein content of less than 0.675 wt %, and
   wherein the said bioactive serum fraction further comprises. a combination of preservatives and stabilizers consisting of a sodium metabisulfite content of 0.20 wt %, potassium sorbate content of 0.10 wt %, sodium benzoate content of 0.10 wt %, tetrasodium EDTA content of 0.25 wt % and pentylene glycol content of 1.90 wt %, by weight of the total composition, and
   wherein the said bioactive serum fraction comprises bioactive properties selected from the group consisting of anti-oxidant activity, anti-inflammatory activity, anti-aging activity, and anti-irritant activity.

2. The bioactive serum fraction according to claim 1, wherein the bioactive serum fraction is derived from the whole ginseng plant, a part of the ginseng plant, or a combination of different parts of the ginseng plant.

3. The bioactive serum fraction according to claim 2, wherein the part of the ginseng plant is selected from the group consisting of rhizome, roots, leaves, stems, flowers, and fruit.

4. The bioactive serum fraction according to claim 1, wherein said serum fraction comprises a total pulegone content of less than 25 ppm.

5. The bioactive serum fraction according to claim 1, wherein said serum fraction comprises a total protein content of less than 0.500 wt %.

6. A product comprising a bioactive serum fraction according to claim 1.

7. The product according to claim 6, wherein said product comprises a leave-on product selected from the group consisting of a cream, a dressing, a gel, a lotion, an ointment, a liquid, a spray applicator, and combinations thereof, or a wash-off product selected from the group consisting of hand dishwashing detergent, liquid hand soap, bar soap, body wash, shampoo, general purpose cleanser, and combinations thereof.

8. The product according to claim 6, wherein said product comprises a functional food or a functional beverage.

9. The product according to claim 6, wherein said product comprises a nutraceutical.

10. A method of using a product comprising the bioactive serum fraction according to claim 1, said method comprising:
    administering the product to a subject under conditions effective to provide anti-inflammatory, anti-irritant, and/or anti-aging activity to the subject.

* * * * *